US00PP24248P3

(12) United States Plant Patent
Olesen

(10) Patent No.: US PP24,248 P3
(45) Date of Patent: Feb. 18, 2014

(54) CLIMBING ROSE PLANT NAMED 'POULCY022'

(50) Latin Name: ***Rosa* hybrid**
Varietal Denomination: Poulcy022

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 48 days.

(21) Appl. No.: 13/507,038

(22) Filed: May 31, 2012

(65) Prior Publication Data

US 2013/0326745 P1 Dec. 5, 2013

(51) Int. Cl.
*A01H 5/00* (2006.01)

(52) U.S. Cl.
USPC ..... Plt./115

(58) Field of Classification Search
USPC ..... Plt./115
See application file for complete search history.

*Primary Examiner* — Kent L Bell

(57) ABSTRACT

A new garden rose plant of the Climbing class which has abundant, medium red flowers and attractive foliage. This new and distinct variety has shown to be uniform and stable in the resulting generations from asexual propagation.

1 Drawing Sheet

Botanical designation: *Rosa* hybrid.
Variety denomination: 'Poulcy022'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulcy022', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant medium red flowers;
2. Vigorous, but compact growth when propagated both as a budded rose and on its own roots;
3. Exceptional disease resistance;
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy022' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcy022' was selected in the spring of 2004 by the inventor as a single plant from the progeny of the aforementioned hybridization.

Asexual reproduction of 'Poulcy022' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcy022' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcy022'.

Specifically illustrated in the drawing are flowers at various stages of development, flower in parts, leaves, and stems.

DETAILED DESCRIPTION OF THE VARIETY

The following is a description of 'Poulcy022', as observed in its growth in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulcy019', U.S. Plant Pat. No. 23,630, are compared to 'Poulcy022' in Chart 1.

CHART 1

| | 'Poulcy022' | 'Poulcy019' |
|---|---|---|
| Petal Count | On average, flowers have 20 petals total, 3 of which are petaloids. | On average, flowers have 25 petals total, 0 to 3 of which are petaloids. |
| Flower Diameter | 55 mm. | 55 mm. |
| General Tonality of Flower Color | Red Group 44B. | Red Group 46A. |

Flower and Flower Bud

Blooming habit: Continuous.
Flower bud:

*Size.*—Upon opening, 30 mm in length from base of receptacle to end of bud. Bud diameter is 13 mm.

*Bud form.*—Lanceolate.

*Bud color.*—As sepals divide petals are Red Group 45A.

*Sepal inner surface.*—Color: Green Group 138B with Orange-Red Group 173A. Surface: Smooth with strong pubescence.

*Sepal outer surface.*—Color: Yellow-Green Group 144A with Greyed-Purple Group 183B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—23 mm long by 8 mm wide.

*Receptacle.*—Texture: Smooth. Size: 7 mm in height by 8 mm wide. Color: Yellow-Green Group 146B. Anthocyanic pigments the color of Greyed-Purple Group 183A observed. Shape: Elliptical.

*Pedicel.*—Surface: Smooth with stipitate glands. Length: 25 to 45 mm. Diameter: 2 to 3 mm on average. Color: Yellow-Green Group 144A with moderate anthocyanic pigments the color of Greyed-Purple Group 183A. Strength: Strong.

*Peduncle.*—Surface: Somewhat rough with small prickles. Length: 3 to 20 cm. Diameter: 3 mm. Color: Yellow-Green Group 144B.

Flower bud development: Flower buds are borne in clusters of 25 to 35 flower buds per flowering branch, in panicle form. Reduced apical dominance in flower habit causes flower buds to develop evenly from the base of the plant to the upper branches.

Flower bloom:

*Fragrance.*—Light floral.

*Duration.*—The blooms have a duration on the plant of approximately 10 days. Petals fall cleanly away from plant after flowers have fully matured.

*Size.*—Flower diameter is 55 mm when open. Flower depth is 23 mm.

*Flower shape.*—General shape is an open cup with petals that curve out from the center.

*Shape of flower, side view.*—Upon opening the upper portion is flat, and the lower portion is flat.

Petalage: Under normal conditions, flowers have 20 petals total, about 3 of which are petaloids.

General tonality of flower: Open flowers are Red Group 44B. There are no changes in tonality as the flower ages.

Petal color:

*Upon opening, outer and inner petals.*—Upper surface: Red Group 44A. Lower surface: Red Group 47B.

*Basal petal spots, upon opening.*—Upper surface: Yellow Group 5A. Lower surface: Yellow Group 5A.

*After opening, inner and outer petals.*—Upper surface: Red Group 44A. Lower surface: Red Group 47B.

*Basal petal spots, upon opening.*—Upper surface: Yellow Group 5A. Lower surface: Yellow Group 5A.

Petals:

*Petal reflex.*—Flat.

*Margin.*—Entire and uniform with an occasional cleft. No undulations of margin observed.

*Shape.*—Generally narrow elliptic. Apex shape: Rounded. Base shape: Acute.

*Size.*—27 mm (l)×25 mm (w).

*Texture.*—Smooth.

*Thickness.*—Average.

Petaloids:

*Size.*—20 mm (l) by 10 mm (w).

*Quantity.*—About 3.

*Shape.*—Asymmetric. The base is acute and the apex is rounded.

*Color.*—Upper surface: Red Group 44A. Lower surface: Red Group 47B. Basal petaloid spots: Upper surface: Yellow Group 5A. Lower surface: Yellow Group 5A.

Reproductive organs:

*Pollen.*—None observed.

*Anthers.*—Size: 2 mm in length. Color: Yellow-Orange Group 21B. Quantity: 70 on average.

*Filaments.*—Color: Orange-Red Group N34A. Length: 5 mm.

*Pistils.*—Length: 4 mm. Quantity: 40 on average.

*Stigmas.*—Color: Yellow-White Group 158A.

*Styles.*—Color: Red-Purple Group 61B.

*Location of stigmas.*—Inferior in location relative to the length of the filaments and the height of the anthers.

*Hips.*—None Observed.

Plant

Plant growth: Arching habit. Plants are 100 cm in height, and 100 cm wide.

Stems:

*Color.*—Juvenile growth: Yellow-Green Group 144B. Mature growth: Yellow-Green Group 144B.

*Length.*—On average, canes are 60 cm from the base of the plant to the flowering portion.

*Diameter.*—7 mm.

*Internodes.*—On mature canes, there is an average distance of 30 mm between nodes.

*Surface texture.*—Young wood: Smooth. Older wood: Rough with moderate amount of small prickles.

Long prickles:

*Incidence.*—9 prickles per 10 cm of stem.

*Size.*—Average length of prickles on mature stems is 6 mm.

*Shape.*—Upper portion is linear. Lower portion is concave.

*Color.*—Juvenile prickles: Greyed-Purple Group 183C. Mature prickles: Greyed-Orange Group 165A.

Plant foliage:

*Compound leaf.*—150 mm (l)×70 mm (w).

*Quantity.*—3 leaves per 10 cm of stem on average.

*Leaf bearing angle to the stem.*—45 degrees.

*Color of juvenile foliage.*—Upper side: Yellow-Green Group 144A. Lower side: Yellow-Green Group 144A. Anthocyanin: Generallized throughout the leaflet, Greyed-Purple Group 183B.

*Color of mature foliage.*—Upper side: Yellow-Green Group 147A. Lower side: Yellow-Green Group 147B.

Plant leaves and leaflets:

*Stipules.*—Size: 23 mm in length. Quantity: 2 per compound leaf. Shape: Linear, slightly broad based with outward extending apices. Margins: Finely serrated. Color: Yellow-Green Group 144A.

*Petiole.*—Length: 30 mm. Diameter: 2 mm.

*Upper surface.*—Color: Yellow-Green Group 146A.

*Lower surface.*—Observations: Few small prickles observed.

*Rachis.*—Length: 55 mm.

*Upper surface.*—Color: Yellow-Green Group 146A.

*Lower surface.*—Observations: Few small prickles observed.

*Leaflet*.—Quantity: Normal number of leaflets per leaf in middle of the stem is 7 leaflets. Margins: Serrated. Size: Average size of the terminal leaflet on normal leaves is 35 mm in length by 22 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Climbing rose class named 'Poulcy022', substantially as illustrated and described herein, due to its abundant medium red flowers, disease resistance, and extended period of bloom.

* * * * *

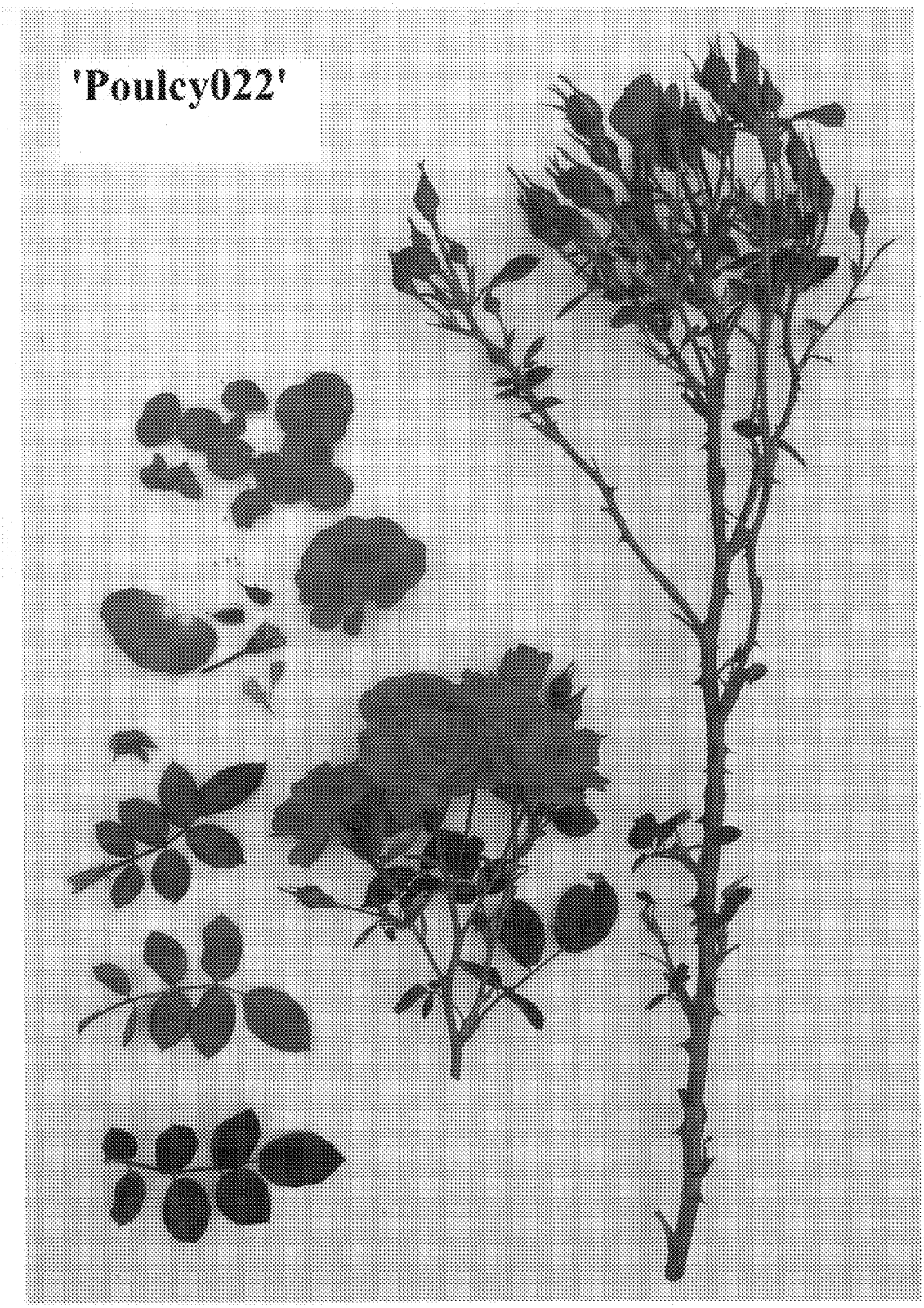
'Poulcy022'